(12) United States Patent
Stopek et al.

(10) Patent No.: US 8,997,978 B2
(45) Date of Patent: Apr. 7, 2015

(54) MEDICAL DEVICE PACKAGE

(75) Inventors: Joshua B. Stopek, Yalesville, CT (US);
Matthew D. Cohen, Berlin, CT (US);
Joseph Hotter, Middletown, CT (US);
William Denman, Winchester, MA (US)

(73) Assignee: Covidien LP, Mansfield, MA (US)

( * ) Notice: Subject to any disclaimer, the term of this patent is extended or adjusted under 35 U.S.C. 154(b) by 790 days.

(21) Appl. No.: 12/544,444

(22) Filed: Aug. 20, 2009

(65) Prior Publication Data

US 2010/0116694 A1   May 13, 2010

Related U.S. Application Data

(62) Division of application No. 11/544,503, filed on Oct. 6, 2006, now abandoned.

(51) Int. Cl.
| | | |
|---|---|---|
| *A61B 17/06* | (2006.01) | |
| *A61B 19/02* | (2006.01) | |
| *A61L 17/00* | (2006.01) | |
| *A61L 27/54* | (2006.01) | |
| *A61L 31/16* | (2006.01) | |
| *A61B 17/00* | (2006.01) | |

(52) U.S. Cl.
CPC ......... *A61B 17/06133* (2013.01); *A61B 19/026* (2013.01); *A61B 2017/00526* (2013.01); *A61B 2017/00893* (2013.01); *A61B 2017/06147* (2013.01); *A61B 2017/06152* (2013.01); *A61B 2019/0274* (2013.01); *A61L 17/005* (2013.01); *A61L 27/54* (2013.01); *A61L 31/16* (2013.01); *A61L 2300/00* (2013.01)

(58) Field of Classification Search
CPC .............. A61B 17/06; A61J 1/00; A61J 1/14; A61J 1/1406; A61J 2001/201
USPC ............ 206/63.3, 438, 524.4, 524.1; 604/416
See application file for complete search history.

(56) References Cited

U.S. PATENT DOCUMENTS

| | | | |
|---|---|---|---|
| 3,369,708 A | * | 2/1968 | Hein .............................. 222/85 |
| 4,259,184 A | | 3/1981 | D'Arnal |
| 4,366,901 A | | 1/1983 | Short |
| 4,424,898 A | | 1/1984 | Thyen et al. |
| 4,699,271 A | | 10/1987 | Lincoln et al. |
| 4,896,767 A | | 1/1990 | Pinheiro |
| 4,961,498 A | | 10/1990 | Kalinski et al. |
| 4,967,902 A | | 11/1990 | Sobel et al. |
| 5,024,322 A | | 6/1991 | Holzwarth |

(Continued)

FOREIGN PATENT DOCUMENTS

| | | |
|---|---|---|
| DE | 4323266 | 1/1994 |
| EP | 0 418 059 A2 | 3/1991 |

(Continued)

OTHER PUBLICATIONS

International Search Report EP 07253902.

(Continued)

*Primary Examiner* — Anthony Stashick
*Assistant Examiner* — Blaine Neway

(57) ABSTRACT

The present disclosure provides a medical device package including a container for receiving a medical device having an area configured for storing at least one agent and a port for permitting the passage of a contact material between the outside the container and the area configured for storing the agent.

9 Claims, 3 Drawing Sheets

(56) References Cited

U.S. PATENT DOCUMENTS

| | | | |
|---|---|---|---|
| 5,038,938 A * | 8/1991 | Berndt | 206/571 |
| 5,052,551 A | 10/1991 | Cerwin et al. | |
| 5,056,658 A | 10/1991 | Sobel et al. | |
| 5,099,994 A | 3/1992 | Kalinski et al. | |
| 5,131,533 A | 7/1992 | Alpern | |
| 5,165,217 A | 11/1992 | Sobel et al. | |
| 5,179,818 A | 1/1993 | Kalinski et al. | |
| 5,180,053 A | 1/1993 | Cascio et al. | |
| 5,192,483 A | 3/1993 | Kilgrow et al. | |
| 5,213,210 A | 5/1993 | Cascio et al. | |
| 5,222,978 A | 6/1993 | Kaplan et al. | |
| 5,228,565 A | 7/1993 | Sinn | |
| 5,230,424 A | 7/1993 | Alpern et al. | |
| 5,236,083 A | 8/1993 | Sobel et al. | |
| 5,246,104 A | 9/1993 | Brown et al. | |
| 5,249,671 A | 10/1993 | Sinn | |
| 5,249,673 A | 10/1993 | Sinn | |
| 5,263,585 A | 11/1993 | Lawhon et al. | |
| 5,271,495 A | 12/1993 | Alpern | |
| 5,275,185 A * | 1/1994 | Florjancic | 134/93 |
| 5,284,240 A | 2/1994 | Alpern et al. | |
| 5,350,060 A | 9/1994 | Alpern et al. | |
| 5,359,831 A | 11/1994 | Brown et al. | |
| 5,366,081 A | 11/1994 | Kaplan et al. | |
| 5,407,071 A | 4/1995 | Lawhon et al. | |
| 5,417,036 A | 5/1995 | Brown et al. | |
| 5,433,315 A | 7/1995 | Brandau | |
| 5,462,162 A | 10/1995 | Kaplan et al. | |
| 5,468,252 A | 11/1995 | Kaplan et al. | |
| 5,472,081 A | 12/1995 | Kilgrow et al. | |
| 5,503,266 A | 4/1996 | Kalbfeld et al. | |
| 5,575,382 A | 11/1996 | Sobel et al. | |
| 5,628,395 A | 5/1997 | Daniele et al. | |
| 5,655,652 A | 8/1997 | Sobel et al. | |
| 5,669,490 A | 9/1997 | Colligan et al. | |
| 5,675,961 A | 10/1997 | Cerwin et al. | |
| 5,681,740 A | 10/1997 | Messier et al. | |
| 5,698,210 A * | 12/1997 | Levy | 424/406 |
| 5,704,469 A | 1/1998 | Daniele et al. | |
| 5,733,293 A | 3/1998 | Scirica et al. | |
| 5,788,062 A | 8/1998 | Cerwin et al. | |
| 5,887,706 A | 3/1999 | Pohle et al. | |
| 5,906,273 A | 5/1999 | Pohle et al. | |
| 5,918,733 A | 7/1999 | Cerwin et al. | |
| 5,954,748 A * | 9/1999 | Totakura | 606/229 |
| 6,016,905 A | 1/2000 | Gema et al. | |
| 6,047,815 A | 4/2000 | Cerwin et al. | |
| 6,076,659 A | 6/2000 | Baumgartner et al. | |
| 6,098,796 A | 8/2000 | Januzeli et al. | |
| 6,105,339 A | 8/2000 | Pohle et al. | |
| 6,135,272 A | 10/2000 | Sobel et al. | |
| 6,135,385 A | 10/2000 | Martinez de Lahidalga | |
| 6,138,440 A | 10/2000 | Gemma | |
| 6,260,699 B1 | 7/2001 | Kaplan et al. | |
| 6,394,269 B1 | 5/2002 | Rudnick et al. | |
| 6,443,949 B2 * | 9/2002 | Altman | 606/41 |
| 6,464,071 B2 | 10/2002 | Baumgartner | |
| 6,481,568 B1 | 11/2002 | Cerwin et al. | |
| 6,481,569 B1 | 11/2002 | Alpern | |
| 6,533,112 B2 | 3/2003 | Warnecke | |
| 6,644,469 B2 | 11/2003 | Alpern | |
| 6,648,133 B1 | 11/2003 | Blaschke et al. | |
| 6,807,737 B1 | 10/2004 | Davia | |
| 2003/0198666 A1 | 10/2003 | Abbas et al. | |
| 2005/0167309 A1 | 8/2005 | Iwatschenko | |
| 2005/0278012 A1 | 12/2005 | Vonderwalde | |
| 2006/0027467 A1 * | 2/2006 | Ferguson | 206/63.3 |
| 2006/0029722 A1 | 2/2006 | Larson et al. | |
| 2006/0069018 A1 * | 3/2006 | Sakai et al. | 514/12 |
| 2006/0163752 A1 | 7/2006 | Wang et al. | |
| 2006/0193884 A1 | 8/2006 | Stopek et al. | |

FOREIGN PATENT DOCUMENTS

| | | |
|---|---|---|
| EP | 0 558 085 A1 | 9/1993 |
| EP | 0 558 086 A1 | 9/1993 |
| EP | 0 564 274 A1 | 10/1993 |
| EP | 0 726 062 A2 | 8/1996 |
| EP | 0 728 445 A1 | 8/1996 |
| EP | 1 275 343 A1 | 1/2003 |
| EP | 1 312 556 | 5/2003 |
| EP | 1 316 291 | 6/2003 |
| GB | 1 327 865 | 8/1973 |
| WO | WO 98/11932 | 3/1998 |
| WO | WO 99/37233 | 7/1999 |
| WO | WO 01/36289 | 5/2001 |
| WO | WO 03/008285 | 1/2003 |
| WO | WO 03/092779 | 11/2003 |
| WO | WO 03/101334 | 12/2003 |

OTHER PUBLICATIONS

International Search Report PCT/US08/002458.
International Search Report PCT/US08/002457.
International Search Report PCT/US07/021421 dated Feb. 26, 2008 (10 pages).

* cited by examiner

MEDICAL DEVICE PACKAGE

CROSS-REFERENCE TO RELATED APPLICATIONS

This application is a divisional of U.S. application Ser. No. 11/544,503 filed Oct. 6, 2006 now abandoned and the disclosures of each of the above-identified applications are hereby incorporated by reference in their entirety.

BACKGROUND

1. Technical Field

The present disclosure relates generally to packaging for medical devices, and more particularly, to a medical device package including a container having an area configured to receive a medical device and an area configured for storing at least one agent and a port for permitting the passage of a contact material between the outside of the container and the area of the container configured for storing the agent.

2. Background of Related Art

Combination medical devices, i.e., medical devices coated with drugs or other bioactive agents, have become more prevalent commercially in recent years. There are many of these combination medical devices known to those skilled in the art. Many of these devices require specialized coatings to facilitate both bioactive agent elution and, more importantly, maintain or enhance the core functionality of the medical device. For example, a suture containing an antimicrobial coating must be able to facilitate the elution of the antimicrobial agent in the coating and also maintain a certain tensile strength, handling ability, knot-tying ability, and degradation rate to ensure the coated suture remains functional as a wound closure device.

Further, with the selection of a new coating, drug or any combination of medical devices comes the challenge of marrying the selected agents with a coating or medical device that can accommodate both technical requirements described above, as well as the manufacturing, sterilizing, and transporting processes involved in producing such products. This often requires the design of new coating polymers, which are specialized to be compatible with a specific agent, as well as new coating, manufacturing, sterilizing and transporting processes. In addition, designing these new coatings and processes creates the added pressures of possibly impacting the shelf-life of the device as well as the end-use of the combination medical device in a negative manner.

Also, medical professionals are limited to using the combination medical device in the dosage and strength produced, without flexibility to alter the product as needed for their respective patients.

Therefore, the present disclosure describes a package for a medical device aimed at simplifying the design and application of combination medical device coatings to provide the following benefits: sensitive agents can be delivered without compromising standard storage or transport conditions; the ability to later combine a specific medical device with agents that were unable to tolerate the required sterilization process for that specific device, under sterile conditions; the medical professional has greater control over product selection; and longer shelf-life of products due to more stable format.

SUMMARY

Accordingly, a package for a medical device in accordance with the present disclosure includes a container for receiving a medical device wherein the container has an area configured for storing at least one agent and a port for permitting the passage of a contact material between the outside of the container and the area of the container configured for storing at least one agent therein. The area configured for storing the agent may be defined within the container or as a separate compartment positioned within or adjacent to the container.

In another embodiment, a medical device package as described herein may include a container configured for receiving a medical device including a reservoir for storing at least one agent and a port for permitting the passage of a contact material between the outside of the container and the reservoir configured for storing the agent. The reservoir is positioned within the container in a manner capable of applying the agent to at least a portion of the medical device received in the container. The portion of the medical device to be contacted by the agent and/or the contact material may pass through or be positioned within the reservoir.

In still another embodiment, a medical device package in accordance with the present disclosure includes a container for receiving a medical device having at least one separate, self-contained agent and a port for permitting the passage of a contact material between the outside of the container and the self-contained agent. It is envisioned that the contact material will interact with the self-contained agent in any manner suitable for activating and/or releasing the agent stored therein so that the medical device received by the container may come in contact with the agent and/or the contact material.

BRIEF DESCRIPTION OF THE DRAWINGS

Various embodiments are described herein with reference to the drawings wherein.

DETAILED DESCRIPTION

Figure 1:
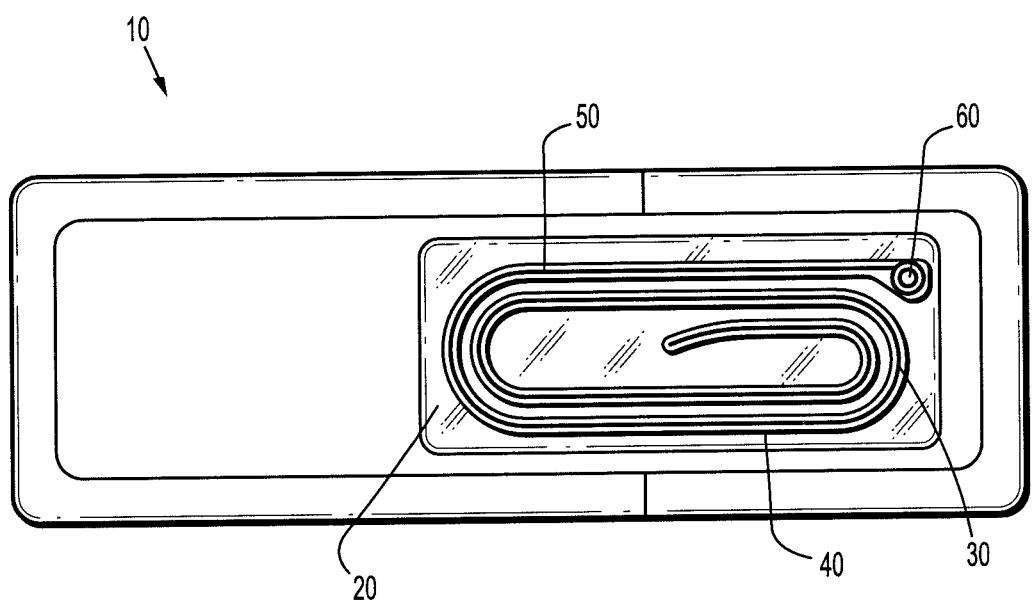
FIG. 1 is a top view of a medical device package described herein, wherein the area configured for storing at least one agent is defined within the container.

The medical device packages described herein include a container having an area configured for receiving a medical device, an area configured for storing at least one agent and a port for permitting the passage of a contact material between the outside of the container and the area configured for storing at least one agent. In some embodiments, the container may include a single area configured for receiving both the medical device and the agent.

It is envisioned that any medical device may be stored within the package. Some examples include, but are not limited to, sutures, staples, clips, adhesives, sealants, stents, grafts, meshes, sternum closures, pins, screws, tacks, and adhesion barriers.

The container is dimensioned and configured to receive a medical device. The container may be any conventional enclosure for storing medical devices and more than one container may be combined to form the medical device packages described herein. Some examples of useful containers include, but are not limited too, pouches, paper retainers, plastic retainers, bags, trays, envelopes, Tyvek® bags, foilpacks, and the like. It is envisioned that the containers may be sealable, non-sealable, breathable, non-breathable, peelable, resealable, and combinations thereof.

The container may be manufactured from any material known to those skilled in the art which is suitable for receiving or storing a medical device. Some examples of suitable materials include, but are not limited to, polycarbonate, high-density polyethylene, polyethylene, polypropylene, thermoplastic resins, polytetrafluoroethylene, ε-caprolactone, glycolide, 1-lactide, d,1-lactide, d-lactide, meso-lactide, trimethylene carbonate, 4,4-dimethyl-1,3-dioxan-2-one, p-dioxanone, dioxepanone, δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, polyolefins, polysiloxanes, polyalkylene glycols, polyacrylates, aminoalkyl acrylates, polyvinylalcohols, polyvinylpyrrolidones, polyoxyethylenes, polyacrylamides, poly(2-hydroxyethylmethacrylate), polymethacrylamide, dextran, alginic acid, sodium alginate, polysaccharides, gelatin and copolymers, homopolymers, and block copolymers thereof.

As further described herein, the container includes an area configured for storing at least one agent. The area for storing the agent is positioned within or adjacent to the package and/or the container in a manner which allows the agent to interact with at least a portion of the medical device. It is envisioned that the agent or agents may be stored in the area configured for storing the agent at any time between the manufacturing of the package and the end-use or withdrawal of the medical device. In some embodiments, the area configured for storing the agent may be intended to keep the agent from prematurely reacting with the medical device prior to use by medical personnel or the introduction of the contact material via the port.

In some embodiments, the area configured for storing the agent may be defined within the container (See FIG. 1). In some embodiments, the area configured for storing the agent may be defined within a portion of the container (See FIG. 2). In still other embodiments, the container may include at least one separate, self-contained agent positioned anywhere within or adjacent to the container (See FIG. 3).

The area configured for storing the agent is capable of storing the agent in any suitable form. The agent may be stored as solid, liquid, semi-solid, gas, or any combination thereof. The at least one agent may be selected from any bioactive and/or non-bioactive agent suitable for combination with the medical device. Suitable agents include, but are not limited to, drugs, such as antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, H$_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents and immunosuppressive agents; coating materials such as lubricants, and non-bioabsorbable substances such as silicone, beeswax, or polytetrafluoroethylene, as well as absorbable substances such as collagen, chitosan, chitin, carboxymethylcellulose, and homopolymers and/or copolymers of polyalkylene glycols, and higher fatty acids or salts or esters thereof, glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxylic acids, and linear aliphatic diols such as butanediol and hexanediol; wound healing agents; adhesives; sealants; blood products; blood components; preservatives; colorants; dyes; ultraviolet absorbers; ultraviolet stabilizers; photochromic agents; anti-adhesives; proteins; polysaccharides; peptides; genetic material; viral vectors; nucleic acids; nucleotides; plasmids; lymphokines; radioactive agents; metals; alloys; salts; growth factors; growth factor antagonists; cells; hydrophobic agents; hydrophilic agents; immunological agents; anti-colonization agents; diagnostic agents; imaging agents; diluents, such as water, saline, dextrose; and combinations thereof.

In addition to the container and the area configured for storing at least one agent, the package includes a port. The port is designed to permit the passage of at least one diluent between the outside of the container and the area configured for storing the agent. It is envisioned that the port may be any type of port or hub, known to allow the passage of a diluent therethrough. The port may be made of any size, shape or dimension and may be composed of any rubber, gel, metallic, polymeric, or thermoplastic material known to those skilled in the art. The port may also be sealable, non-sealable, resealable, stationary, movable, peelable, self-puncturable and combinations thereof.

The port may be positioned along any side, edge or corner of the container. In embodiments wherein the package includes more than one container, the port may be positioned along any side, edge or corner of any of the containers included in the package. In addition, the package may contain more than one port and/or more than container may share a common port.

In some embodiments, the port may be an injectable-hub, or injection port, which is designed to remain sealed by self-sealing action to ensure no liquid, semi-solid, or gas medium can escape and also so no pathogens can breach the container. In some embodiments, the port may be a hub designed in such a way that only a particular injector can mate with the port, i.e., male/female or lock/key type hubs. These types of ports provide more safety to the user of the port because the port does not necessarily require the use of a sharp injector or needle.

The contact material is intended to be delivered from outside the container, via the port, to the area configured for storing at least one agent. In embodiments where the container includes at least one agent, the contact material may be introduced to initiate or enhance the interaction, penetration, impregnation, or coating of the medical device by the stored agent. The term "contact material" is meant to include any material, i.e., solid, liquid, semi-solid, gas, or combination thereof which interacts with the agent, the medical device, or the container itself. In some embodiments, the contact material may be any of the bioactive or non-bioactive agents described herein. In particularly useful embodiments, contact materials include diluents or wetting agents, such as water, saline, dextrose and lactated ringers.

Turning now to FIG. 1, package 10 is shown including container 20 having a single area 40 configured for storing at least one agent and receiving the medical device, and a port 60 for permitting the passage of a contact material between the outside of container 20 and area 40 configured for storing the agent. In some embodiments, at least a portion of medical device 30, i.e., a suture, may be in contact or coated with an agent 50 prior to be received and stored within container 20. Port 60 is positioned on an outer edge of container 20 and is connected to area 40. It is envisioned that an injector may be connected to port 60 to deliver a contact material through port 60 and into area 40 to interact with agent 50. Since at least a portion of medical device 30 is positioned within area 40, the contact material and agent 50 may coat, impregnate, react with, or be absorbed by medical device 30.

Figure 2B:
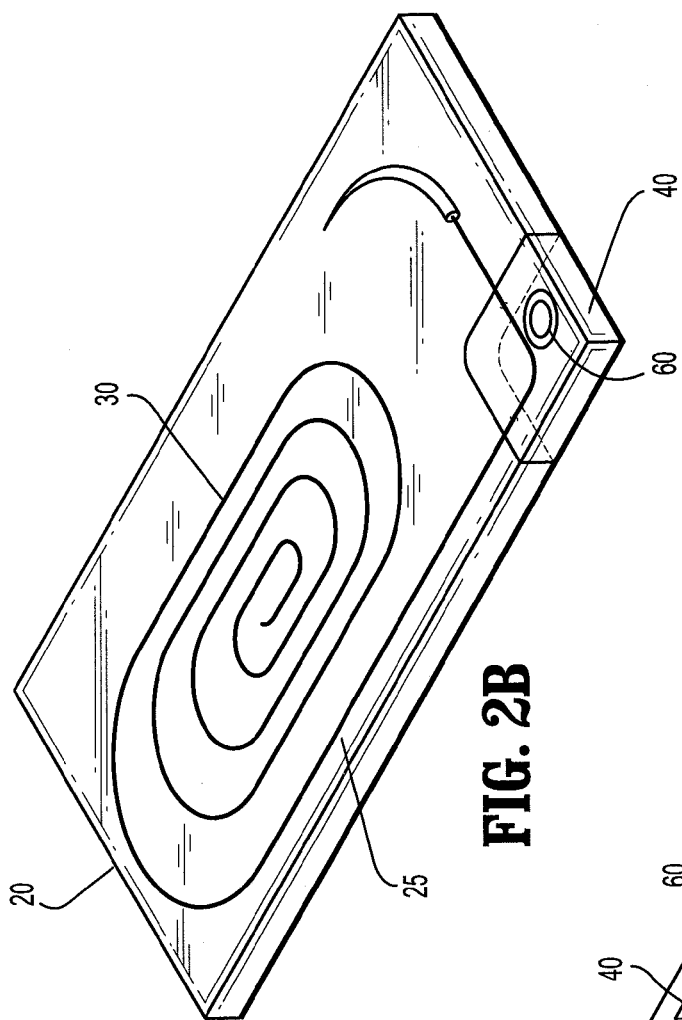
FIG. 2 is a perspective view of a medical device package described herein, wherein the area configured for storing at least one agent is a compartment defined within a portion of the container.
Figure 2A:
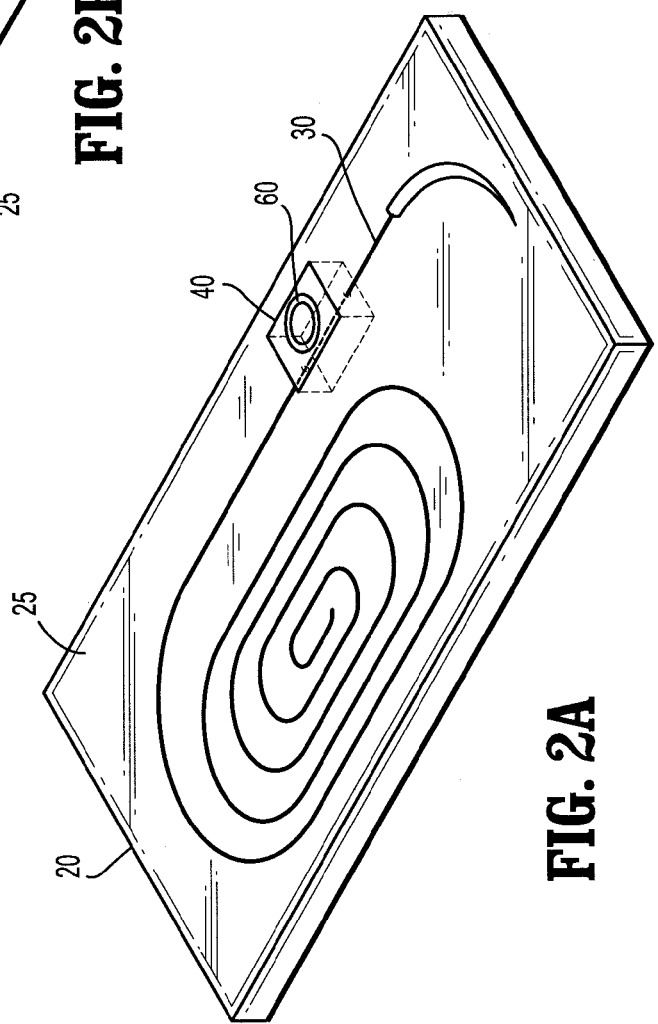

In another embodiment, as shown in FIG. 2, container 20 includes an area configured for receiving a medical device 25, an area configured for storing at least one agent 40 and a port 60. The area configured for storing an agent 40 is shown as a reservoir or compartment positioned within container 20. In some embodiments, the reservoir or compartment may be designed as a hollow chamber configured for storing agent 50. In some other embodiments, the reservoir may be used to apply agent 50 to specific portions of medical device 30. In still other embodiments, the reservoir may be used to apply agent 50 to at least a portion of medical device 30 as it is withdrawn from container 20.

It is also envisioned that the reservoir may be detachable or removable from container 20. It is envisioned that the reservoir is capable of storing from about 0.01 microliters to about 10,000 microliters. In some embodiments, the reservoir 40 does not contain an agent. Rather, an agent or a contact material or both may be added to reservoir 40 via port 60 by the end-user of the medical device immediately prior to withdrawal of the medical device.

Figure 3:
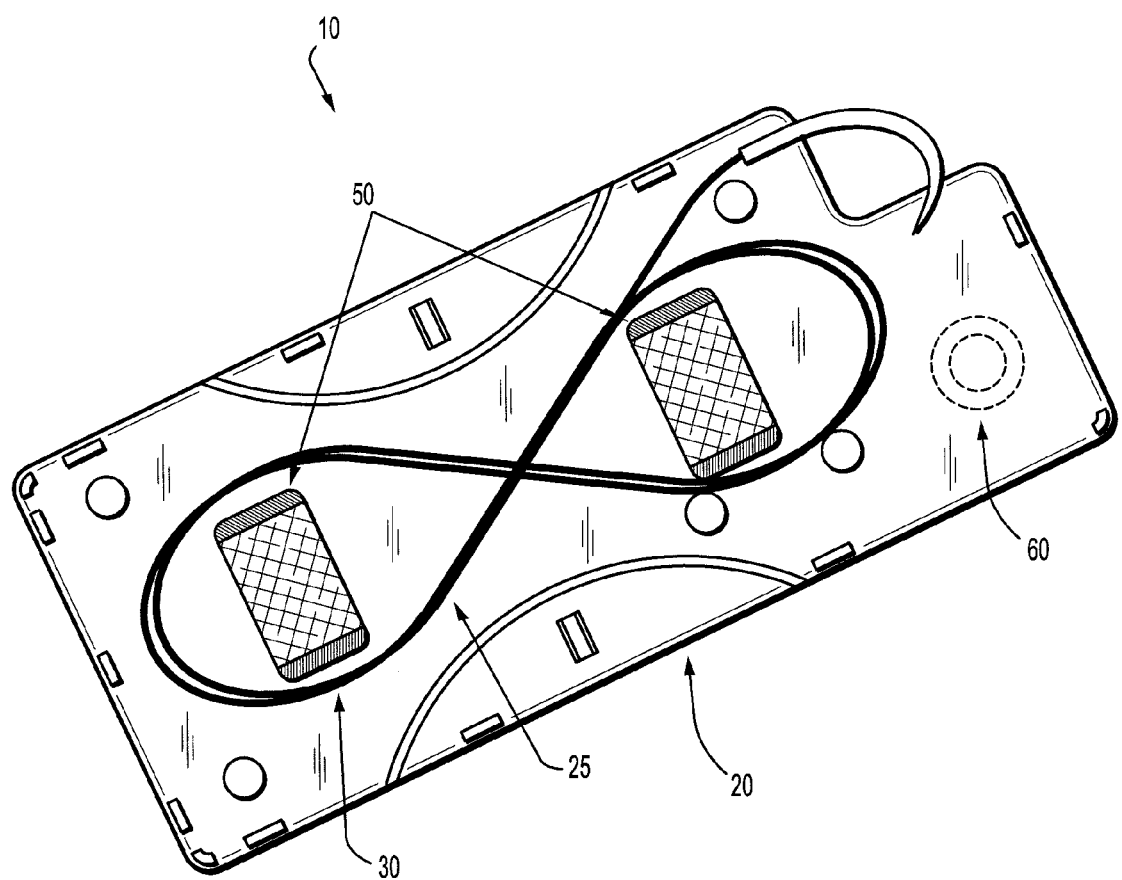
FIG. 3 is a perspective view of a medical device package described herein, wherein at least one separate, self-contained agent is positioned within the container.

Turning now to FIG. 3, package 10 is shown including container 20 having an area configured for receiving a medical device 25, at least one separate, self-contained agent 50 and a port 60. It is envisioned that the self-contained agent is capable of being dissolved, reconstituted, emulsified, suspended, vaporized, melted, and the like, by the contact material to initiate or enhance the interaction, penetration, impregnation, or coating of the medical device. In some embodiments, the self-contained agents may take the form of or be stored within capsules, tablets, pellets, particulate matters, pressed powders, organized gels, and the like. The self-contained agents may include materials such as gelatin, polyvinyl alcohols, hydrophilic, hydrophobic, and amphiphilic materials. As shown in FIG. 3, a pair of self-contained agents 50, in the form of gelatin capsules, will not interact with medical device 30 until the introduction of a contact material via port 60. Port 60 is capable of permitting the passage of the contact material between the outside of the container and self-contained agents 50

It is well understood that various modifications may be made to the embodiments disclosed herein. Therefore, the above description should not be construed as limiting, but merely as exemplifications of particularly useful embodiments. Those skilled in the art will envision other modifications within the scope and spirit of the claims appended hereto.

What is claimed is:

1. A medical device package comprising:
   a medical device;
   at least one solid self-contained agent in a form selected from the group consisting of capsule, tablet, pellet, and pressed powders;
   a container having an area configured for receiving the medical device, and the at least one solid self-contained agent; and
   a port for permitting the sterile passage of a contact material between the outside of the container and the at least one solid self-contained agent.

2. The medical device package of claim 1 wherein the medical device is selected from the group consisting of sutures, staples, clips, grafts, stents, meshes, sternum closures, pins, screws, tacks, and combinations thereof.

3. The medical device package of claim 1 wherein the medical device is a suture.

4. The medical device package of claim 1 wherein the at least one solid self-contained agent is selected from the group consisting of drugs, coating materials, wound healing agents, adhesives, sealants, blood products, blood components, preservatives, colorants, dyes, ultraviolet absorbers, ultraviolet stabilizers, photochromic agents, anti-adhesives, proteins, polysaccharides, peptides, genetic material, viral vectors, nucleic acids, nucleotides, plasmids, lymphokines, radioactive agents, metals, alloys, salts, growth factors, growth factor antagonists, cells, hydrophobic agents, hydrophilic agents, immunological agents, anti-colonization agents, diagnostic agents, imaging agents, radiopaque agents, and combinations thereof.

5. The medical device package of claim 1 wherein the at least one solid self-contained agent is a drug.

6. The medical device package of claim 5 wherein the drug is selected from the group consisting of antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents, immunosuppressive agents and combinations thereof.

7. The medical device package of claim 1 wherein the at least one self-contained agent is a capsule.

8. The medical device package of claim 7 wherein the capsule is made from a polyvinyl alcohol.

9. The medical device package of claim 1 wherein the port is an injection port.

* * * * *